(12) United States Patent
Long

(10) Patent No.: US 8,647,267 B1
(45) Date of Patent: Feb. 11, 2014

(54) FOOD AND DIGESTION CORRELATIVE TRACKING

(71) Applicant: Sarah Long, Denver, CO (US)

(72) Inventor: Sarah Long, Denver, CO (US)

(*) Notice: Subject to any disclaimer, the term of this patent is extended or adjusted under 35 U.S.C. 154(b) by 0 days.

(21) Appl. No.: 13/737,545

(22) Filed: Jan. 9, 2013

(51) Int. Cl.
*A61B 5/00* (2006.01)
*G06F 19/00* (2011.01)
*G06K 9/62* (2006.01)
*G06Q 50/22* (2012.01)
*G06Q 50/24* (2012.01)

(52) U.S. Cl.
CPC .............. *G06F 19/30* (2013.01); *G06F 19/34* (2013.01); *G06F 19/363* (2013.01); *G06F 19/3487* (2013.01); *G06K 9/62* (2013.01); *G06Q 50/22* (2013.01); *G06Q 50/24* (2013.01); *A61B 5/411* (2013.01); *A61B 5/0002* (2013.01); *A61B 5/00* (2013.01); *A61B 2505/07* (2013.01); *Y10S 715/961* (2013.01)
USPC .................. 600/300; 705/2; 705/3; 707/723; 707/748; 707/751; 707/758; 715/700; 715/961

(58) Field of Classification Search
None
See application file for complete search history.

(56) References Cited

U.S. PATENT DOCUMENTS

| | | | | |
|---|---|---|---|---|
| 4,414,629 | A * | 11/1983 | Waite | 705/28 |
| 6,641,532 | B2 * | 11/2003 | Iliff | 600/300 |
| 6,712,763 | B2 * | 3/2004 | Abraham-Fuchs et al. | 600/300 |
| 7,613,619 | B1 * | 11/2009 | Harter et al. | 705/2 |
| 8,234,124 | B2 * | 7/2012 | Canu et al. | 705/2 |
| 2002/0035486 | A1 * | 3/2002 | Huyn et al. | 705/3 |
| 2004/0091843 | A1 * | 5/2004 | Albro et al. | 434/127 |
| 2004/0122706 | A1 * | 6/2004 | Walker et al. | 705/2 |
| 2007/0179354 | A1 * | 8/2007 | Stupp et al. | 600/300 |
| 2008/0183047 | A1 * | 7/2008 | Geraci et al. | 600/300 |
| 2009/0030290 | A1 * | 1/2009 | Kozuch et al. | 600/301 |
| 2011/0166881 | A1 * | 7/2011 | Brazzo et al. | 705/3 |
| 2011/0225114 | A1 * | 9/2011 | Gotthardt | 706/50 |
| 2011/0276344 | A1 * | 11/2011 | Williams | 705/2 |
| 2011/0318717 | A1 * | 12/2011 | Adamowicz | 434/127 |
| 2013/0085345 | A1 * | 4/2013 | Geisner et al. | 600/300 |
| 2013/0105565 | A1 * | 5/2013 | Kamprath | 235/375 |

FOREIGN PATENT DOCUMENTS

WO     WO 2007069118 A2 *  6/2007

OTHER PUBLICATIONS

Alpay, K. et al; "Diet restriction in migraine, based on IgG against foods: A clinical double-blind, randomised, cross-over trial"; 2010; Cephalalgia 30(7) 829-837.*

Galland, L. "Food Allergies Cause Migraine Headaches"; 2011, p. 1-4; http://pilladvised.com/2011/01/food-allergies-cause-migraine-headaches/.*

Ortolani, C. et al; "Study of nutritional factors in food allergies and food intolerances"; Luxembourg: Office for Official Publications of the European Communities; p. 1-204.*

FDA: Center for Food Safety and Applied Nutrition; "Approaches to Establish Thresholds for Major Food Allergens and for Gluten in Food", 2006, p. 1-108.*

(Continued)

*Primary Examiner* — Bill Thomson
*Assistant Examiner* — Marie Archer
(74) *Attorney, Agent, or Firm* — Maschoff Brennan

(57) ABSTRACT

Embodiments of the invention include methods and systems for correlating relationships between foods and symptoms such as gastrointestinal manifestations. Users can provide information regarding food intake and/or symptoms through any number of devices. The food and/or symptoms can be analyzed to pinpoint foods that are highly correlated with health symptoms, such as, digestive problems. Removal of such foods from the user's diet can then be suggested.

21 Claims, 7 Drawing Sheets

(56) References Cited

OTHER PUBLICATIONS

Lueck, K.; "The Dietary Migraine: How Food Can Cause Headaches"; Nutrition Bytes 3(1); 1997, p. 1-4.*

MacGregor, A. "Food Allergy Tests and Migraine", Migraine News, Issue 94; 2006; p. 6-7.*

Grant, C. G.; "Food Allergies and Migraine"; The Lancet; May 5, 1979; p. 966-967.*

Mobile_App_Food_Allergy_Detective_Specifications_2010; 2010; p. 1-3.*

* cited by examiner

FOOD AND DIGESTION CORRELATIVE TRACKING

BACKGROUND

Irritable bowel syndrome (IBS) is a malady suffered by an estimated 20% of the population. IBS is a symptom-based diagnosis characterized by chronic abdominal pain, discomfort, bloating, and/or alteration of bowel habits. Diarrhea and/or constipation are typical symptoms of IBS. There are no known cures of IBS. Various other digestive symptom-based maladies also inflict many and may not have a cure.

BRIEF SUMMARY

Embodiments of the invention are directed toward food and symptom correlative tracing. In doing so, embodiments of the invention can help users identify foods that contribute to various symptoms, for example, symptoms related to IBS.

Embodiments of the invention include a method that receives a plurality of indications from a user specifying ingestion of particular foods along with the time the foods were ingested and/or the quantity of food ingested. The particular food can then be recorded in a database with the time the food was ingested. An indication can also be received from a user specifying a symptom along with the time the symptom occurred and/or related descriptive details; and the symptom can be recorded in the database with the time the symptom occurred. The method can also analyze the database to determine whether any of the foods are highly correlated with the occurrence of the symptom.

Some embodiments the method can determine whether any of the foods ingested within zero to seventy-two hours prior to the symptom are highly correlated with the symptom. In some embodiments the method can determine whether any of the foods ingested within zero to seventy-two hours prior to the symptom are known to be highly correlated with food allergies. In some embodiments foods ingested within zero to seventy-two hours prior to the symptom can be flagged.

Some embodiments of the invention include a computer system (e.g., server) that includes a processor, a database, a network interface, and a non-transitory computer-readable medium embodying program components that configure the computing system to perform the method or methods described above.

Some embodiments of the invention include a computer program product comprising a non-transitory computer-readable medium embodying code executable by a computing system. The computer readable medium can include code for providing a user interface listing a plurality of foods; receiving an indication from the user through the user interface specifying a particular food listed in the listing and indicating that the food was ingested by the user; providing a user interface listing a plurality of symptoms; and receiving an indication from the user through the user interface specifying a particular symptom listed in the listing as affecting the user.

Some embodiments of the invention include a method that identifies a symptom in a database comprising a plurality of symptoms entered by a user and the time the symptom occurred. Another symptom can be identified in the database, where this other symptom occurred in time after the first symptom. The method can determine whether a pattern exists between the two symptoms and possible other symptoms. The method can also determine whether the first symptom is a trigger symptom.

BRIEF DESCRIPTION OF THE DRAWINGS

Illustrative embodiments of the present invention are described in detail below with reference to the following drawing figures.

DETAILED DESCRIPTION

Embodiments of the invention include methods and systems for correlating relationships between foods and symptoms such as gastrointestinal manifestations. Users can provide information regarding food intake and/or symptoms through any number of devices. The food and/or symptoms can be analyzed to pinpoint foods that are highly correlated with health symptoms, such as, digestive problems. Removal of such foods from the user's diet can then be suggested. While embodiments of the invention are described in relation to food intake, such food intake can include anything ingested such as drink or medicine. Moreover, while digestive maladies and/or symptoms are discussed and/or correlated with food intake, any type of health issue or symptom can be tracked and/or correlated with food intake. Moreover, embodiments of the invention may also extend to any medical or health investigation and/or trial.

Figure 1:
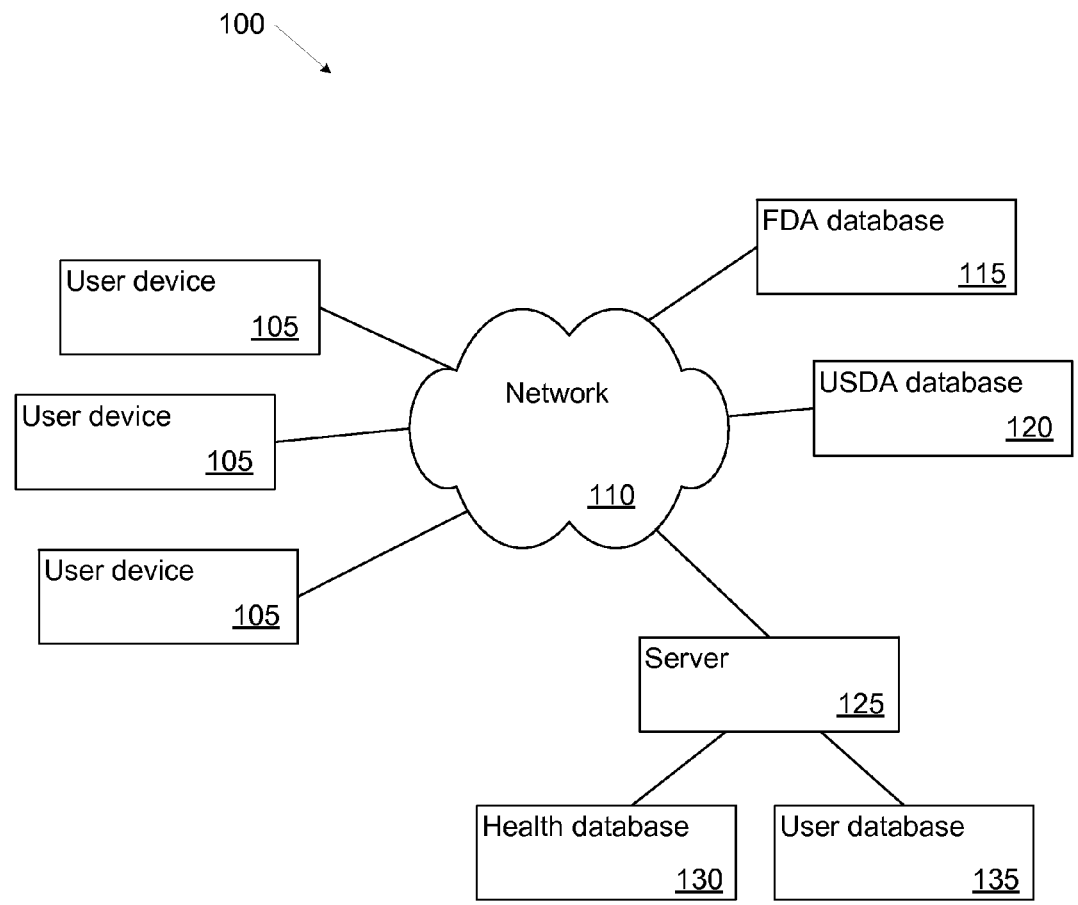
FIG. 1 shows a block diagram of a system that can be used in embodiments of the invention.

FIG. 1 shows a block diagram of system 100 that can be used in embodiments of the invention. Users can send and/or receive data through any number of user devices 105. User devices can include smart phones, tablets, and/or personal computers. Access can occur through a web-based application, a dedicated application, and/or a dedicated app. For example, an app can include an app downloaded from the iTunes® or Android® store.

User devices 105 can connect with server 125 through network 110. Network 110 can include a wired and/or a wireless network; for example, the Internet. Server 125 can include one or more servers and/or may include a cloud server, multiple distributed servers, and/or any other combinations of servers. Server 125 can be any computing device that can communicate with other devices through network 110.

Server 125 can include and/or be coupled with any number of databases either directly as shown with databases 130 and 135 or through a network as shown with database 115 and 120, regardless of whether the databases are shown as connected through the network or directly. Health database 130 can include data correlating food with allergies and/or symptoms. User database 135 can include user data. User data can be sent from user devices 105 and/or data from other databases. FDA database 115 can be a database from the U.S.

Food and Drug Administration that includes information about the ingredients and nutritional content of food items, processed foods, and prepared food, among other data. USDA database 120 can be a database from the U.S. Department of Agriculture National Nutrient Database among other data. Various other databases can be included.

These databases can include information that can be used, for example, by server 125 to correlate food intake with known symptoms. Any number of symptoms, manifestations, and/or maladies can be tracked and/or correlated with food intake. These data stored within server 125 can include data about, for example, food allergies (e.g., celiac disease), food intolerances, food sensitivities, irritable bowel disease, irritable bowel syndrome (IBS), cholecystectomy, infections (e.g., candida, bacterial, viral, fungal, parasitic), microscopic colitis, malabsorption syndrome (e.g., gluten intolerance, lactose intolerance, Small Intestine Bacterial Overgrowth), maldigestion, pancreatic issues, digestive enzymes, bile production, acid reflux, etc.

Any number of symptoms can be tracked, including, for example abdominal bloating, cramping, abdominal distension, excessive gas, diarrhea, constipation, loose stools, fatty stools, tarry stools, passage of mucous, incomplete evacuation, anal leakage, headaches, lethargy, skin rashes, joint pain, etc. Other symptoms can be tracked, for example, those symptoms related to the small bowel, large bowel, and any part of the digestive track where food or drink causes gastrointestinal discomfort, upset, or otherwise unusual behavior for each patient.

User devices 105 can be used primarily to track food intake, track symptoms, and/or provide information to the user. This can be done by providing a user interface that allows a user to provide information about their food intake and/or their symptoms. The user interface can also provide information to the user. This user interface can include various dropdown menus, radio buttons, text fields, etc. to elicit the user input.

Figure 2:
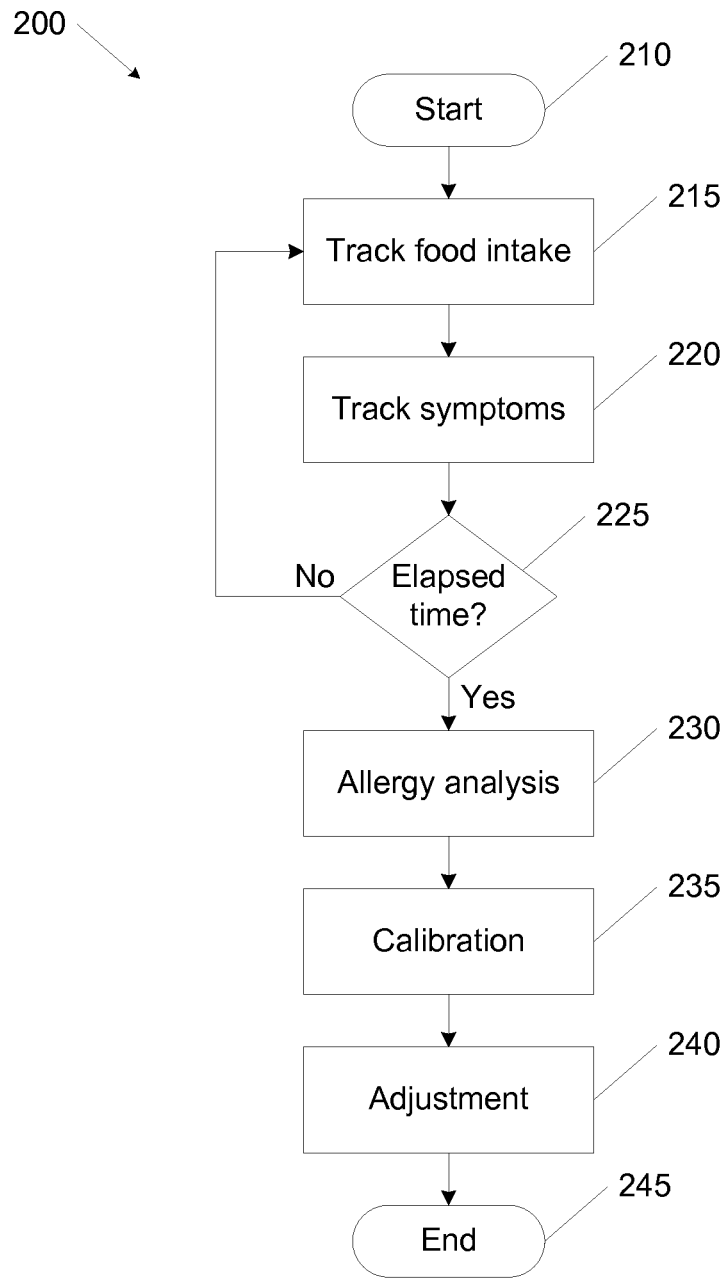
FIG. 2 shows a flowchart of a process for tracking food intake and symptoms according to some embodiments of the invention.

FIG. 2 shows a flowchart of process 200 for tracking food intake and symptoms according to some embodiments of the invention. While process 200 starts at block 210, various initializations can occur at the beginning of the process. For example, the user can log in or be automatically logged in to access their account. If this is the first time the user has logged in, an account may be created and/or a health questionnaire can be presented to the user and health related data returned by the user. The health questionnaire can present a series of questions that a user can respond to, to input information about their general health. In some embodiments the health questionnaire can be presented to users at certain time periods in order to update the user's health information.

At block 215 the user's food intake can be tracked. The tracking of food intake can occur over a period of time. User device 105 can provide an interface that allows a user to enter information about their food intake.

In some embodiments, food groups can be presented that allow the user to isolate the foods eaten. For example, a base interface can list foods such as meat, dairy, drink, vegetable, fruit, dessert, and bread. If the user selects fruit, a listing of different fruits can be provided. If the user selects meat, then a listing of meat can be provided. Foods can also be listed based on prepared foods such as lasagna, soups, sandwiches, enchiladas, hamburger, etc. The user may also be provided with an interface to indicate the quantity of the food. The user can also be provided with an interface to indicate how the food was cooked; for example, raw, boiled, baked, deep fried, broiled, etc. The information provided by the user can be sent to server 125 through network 110.

In some embodiments, the user can indicate that they are eating at a specific restaurant, and the restaurant's menu can be displayed. The user can then select the food they ate. As yet another example, a GPS device can be used to indicate that the user is eating at a restaurant and the menu can be automatically provided through the user interface. Various other techniques can be used to provide a selectable user interface where a user can enter food intake.

At block 220 the user's symptoms can be tracked, for example, using user device 105. Symptom tracking can also occur over a period of time. The user interface can also be used to elicit details from a user about specific symptoms. A number of examples are shown in the chart below. For example, the user can be queried whether they have any of the digestive activity to record shown in the column listed as "digestive activity." When that option is selected by the user, then more detail can be requested by asking the user to select any of the symptoms or enter data about frequency or duration of the symptom. Similarly, additional symptom queries can be made as well as shown in the chart. Any number of additional details can be queried about a symptom.

| Digestive Activity | Symptom | Additional symptom description |
|---|---|---|
| Abdominal Symptoms | Bloating Distension Cramping Frequency Duration | |
| Digestive symptoms | Excessive gas Frequency Duration | |
| Regular Bowel Movement | No additional symptoms After constipation Post movement symptoms Frequency Duration | Post bowel movement anal leakage Feeling of incomplete evacuation Passage of mucous |
| Irregular Bowel Movement | Loose stool Diarrhea Explosive diarrhea Fatty stool Tarry stool [this should have a pop-up warning about blood in stool and to contact doctor] Passage of mucous only Frequency Duration | Post bowel movement anal leakage Feeling of incomplete evacuation Passage of mucous |

Food intake and symptoms can be tracked for a set period of time. At block 225 process 200 can determine if a predetermined period of time has elapsed for the collection of food intake and symptom data from blocks 210 and 215. This period of time can be any period of time, for example, one, two, three, four, five, or six months. Of course, the longer the period of time the larger the collected data set and the more likely the data will capture a symptom-food correlation. But shorter periods of time are more likely to be more user friendly.

Figure 3:
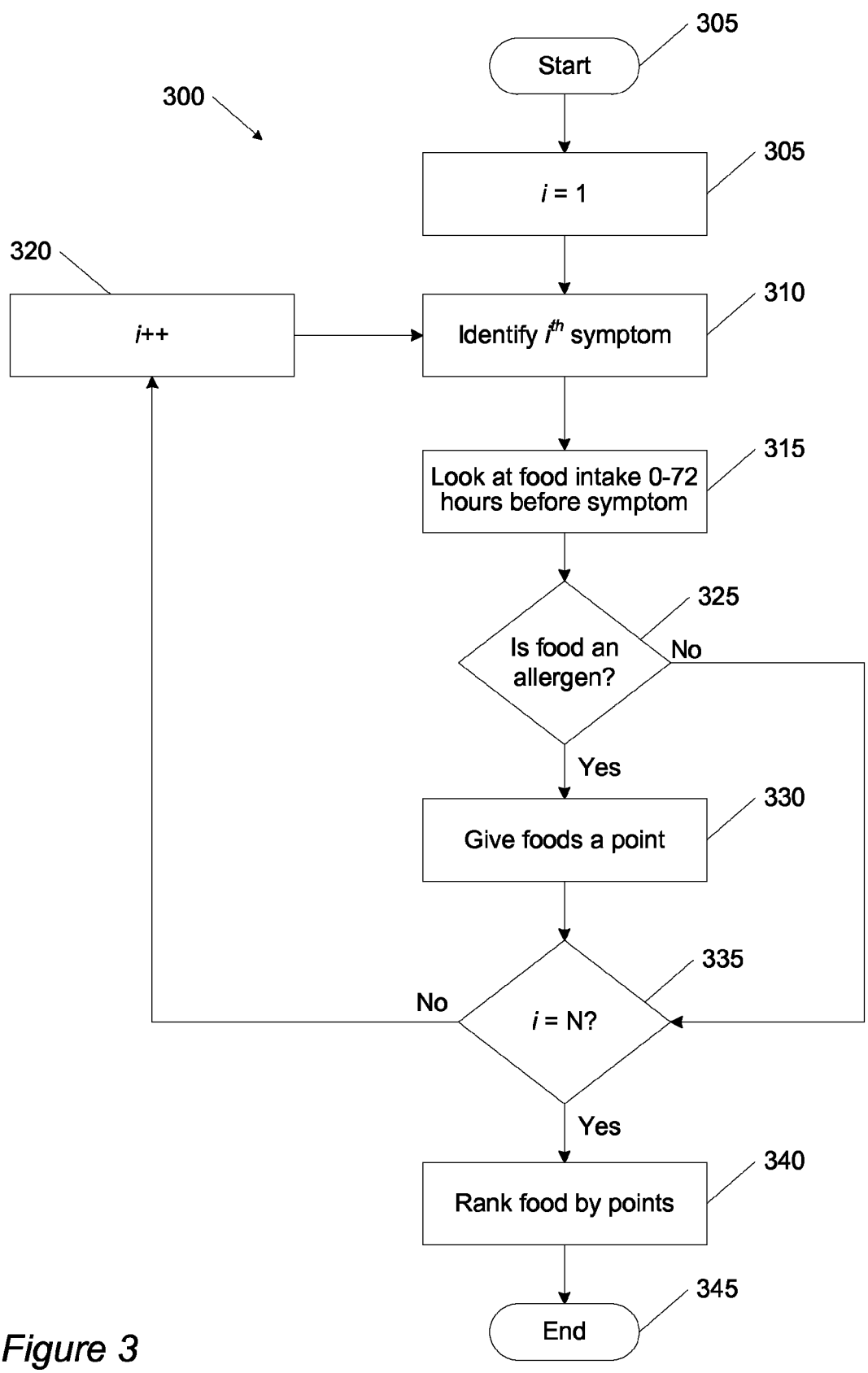
FIG. 3 is an example of a process for determining if an episode can be correlated with allergies according to some embodiments of the invention.

At block 230 an allergy analysis of the data can occur to determine if any symptoms can be correlated with foods known to be highly correlated with food allergies. These foods can include, for example, dairy, eggs, wheat, soy, shellfish, fish, corn, peanuts, tree nuts, etc. Various other foods can be included. These foods may also depend on information provided by the user's health questionnaire. The first analysis can scroll through the listing of symptoms and identify every symptom that is irregular. Then it can look to see if any foods known to be highly correlated with food allergies have been consumed within the previous 0 to 72 hours. In some embodiments, the time period can be 0-3, 3-6, 3-12, 12-24, 24-72, 24-48, 48-72, 12-72, 48-120, 48-144, 48-168, 72-120, 72-144 and/or 72-168 hours. If so, the foods can be given a point. Moreover, if a pattern is discovered that such foods repeatedly result in symptoms, the foods can be repeatedly given a point. Medications can also be analyzed to see if any medicines are highly correlative with allergies. FIG. 3 is another example of a process for determining whether episodes can be correlated with allergies.

Figure 4:
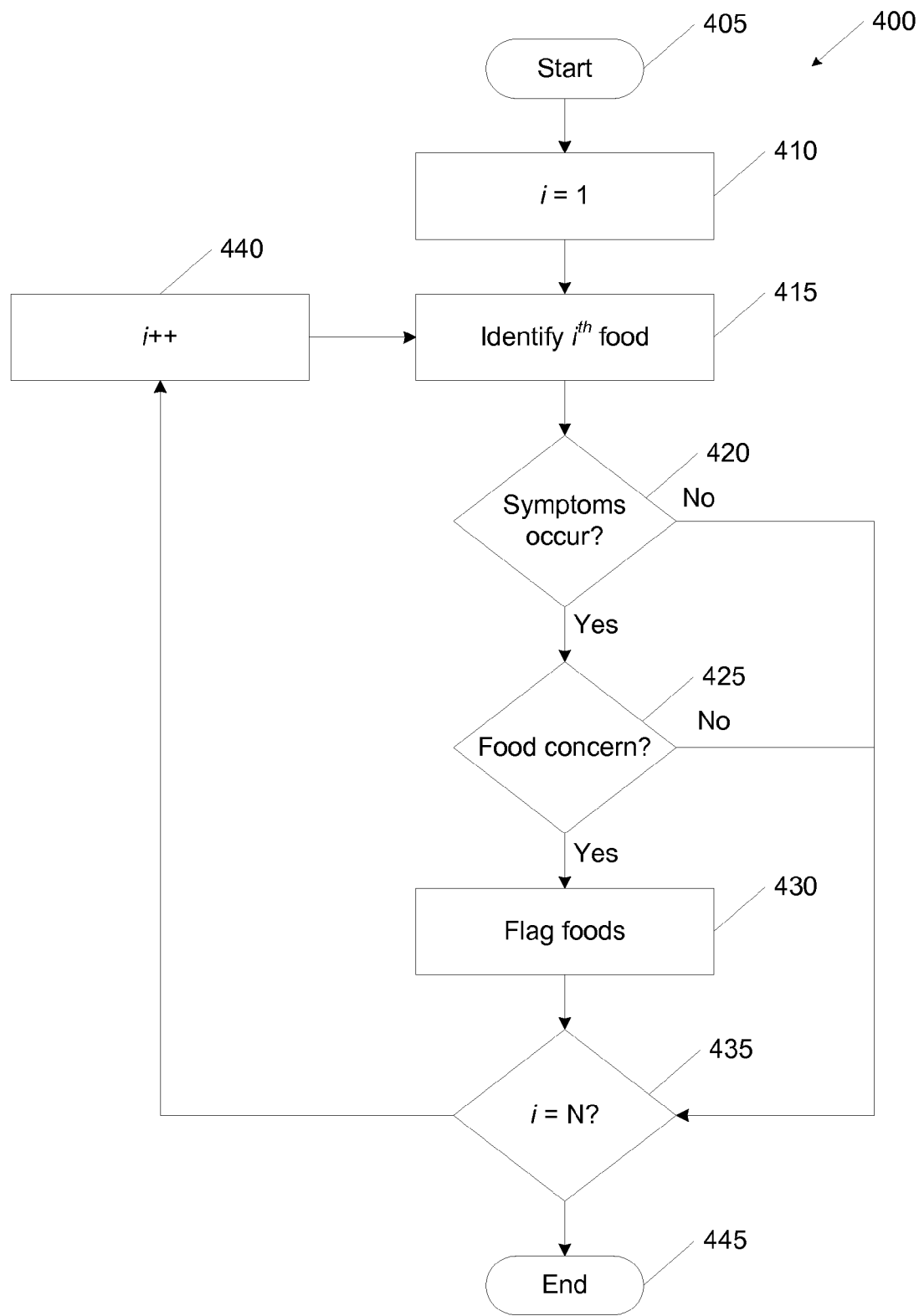
FIG. 4 is a flowchart of a process for calibration, which analyzes the collected data and flags ingested foods as potential causes of symptoms according to some embodiments of the invention.

At block 235 process 200 can undergo calibration where the data entered through the process can be analyzed and foods that are correlated with symptoms can be given one or more points. Process 400 shown in FIG. 4 is an example of a calibration. The term allergy can also be used to refer to intolerances and/or sensitivities.

At block 240 adjustment can occur. Adjustment is a process where foods flagged or given a point during calibration can be tested to determine whether the food is highly correlated with symptoms. Whereas calibration operates on food data collected earlier, adjustment occurs in real-time as food is being ingested and/or as symptoms occurs. Moreover adjustment can use the points given to food during calibration. It can also remove user known allergy food and/or symptoms relationships from the data set to identify unknown relationships.

After adjustment process 200 can end at block 245. In some embodiments calibration and/or adjustment can be repeated any number of times. Moreover, any block or step singularly or in combination with other blocks or steps can be repeated prior to ending process 200. Moreover, any the blocks or steps shown in process 200 can occur in any order.

FIG. 3 is an example of process 300 for determining if symptoms can be correlated with allergies according to some embodiments of the invention. The term allergy can be used to refer to intolerances and/or sensitivities. These allergies can be food or non-food related, including medicine, for example. Process 300 can start at block 305. At block 310 counter i can be initialized. Process 300 then iteratively looks through the collected data associated with symptoms; for example, the data collected at block 220 in FIG. 2. The $i^{th}$ symptom can be selected at block 310.

At block 315 foods for the previous 0 to 72 hours can be reviewed. In some embodiments, the time period can be 0-3, 3-6, 3-12, 12-24, 24-72, 24-48, 48-72, 12-72, 48-120, 48-144, 48-168, 72-120, 72-144 and/or 72-168 hours. At block 325 these foods can be reviewed to determine if they are highly correlated with food allergies. This can be done, for example, by comparing food entered at block 215 of FIG. 2 with a list of foods known to be highly correlated with food allergies. At block 330 foods that are found to be highly correlated with food allergies are given a point at block 325. In some embodiments foods that are found to be highly correlated with food allergies are given more than one point. If the foods are not correlated with then process 300 can proceed to block 335.

At block 335 it can be determined if there are still symptoms to analyze (e.g., i≤N, where N is the number of symptoms in the database) then process 300 proceeds to block 320. Otherwise, process 300 moves to block 340 where foods are ranked by the points assigned at block 330. Process 300 can end at block 345. In some embodiments, rather than ranking the foods by points, process 300 can identify foods that have been given points greater than a threshold value. The threshold value can depend, for example, on the period of time data was gathered, the number of symptoms reported, etc.

Any block or step singularly or in combination with other blocks or steps can be repeated prior to ending process 300. Moreover, any the blocks or steps shown in process 300 can occur in any order.

FIG. 4 is a flowchart of process 400 for calibration, which analyzes the collected data and flags ingested foods as potential causes of symptoms according to some embodiments of the invention. In some embodiments, process 400 can be performed, for example, by server 125 using data stored in user database 135. In some embodiments, process 400 can be performed, for example, on user device 105. The data can include a history of ingested food, including the quantity of food ingested, and/or a history of recorded digestive symptoms. Process 400 starts at block 405. At block 410, a process counter can be initialized; for example, i=1. Any counter or process can be used to systematically work through the collected data.

At block 415 process 400 can pull the $i^{th}$ food item recorded in the database. At block 420 process 400 can identify whether any symptoms followed ingestion of the $i^{th}$ food item. Process 400 can identify any symptoms that have occurred within 0 to 72 hours after ingestion of the $i^{th}$ food. In some embodiments, the time period can be 0-3, 3-6, 3-12, 12-24, 24-72, 24-48, 48-72, 12-72, 48-120, 48-144, 48-168, 72-120, 72-144 and/or 72-168 hours. If symptoms have not occurred process 400 proceeds to block 435.

If symptoms occurred then process 400 moves to block 425 and determines whether the food item is a food concern. The process can be run for a food concern where the food is known to be highly correlated with food allergies or digestive maladies. Or the process can be run where any foods are considered for correlation. A food concern can be any food determined in block 230 of process 200 shown in FIG. 2 to be foods that may produce a symptom. If the food is a food concern, then the food is given a point at block 430, otherwise process 400 moves to block 435.

At block 435 process 400 can determine whether all the foods in the database have been analyzed by determining whether the counter has reached the number of foods, N, in the database. If the end of the database has not been reached, then process 400 proceeds to block 440 where the counter is incremented, and then proceeds to block 415. If the end of the database has been reached, then process 400 ends at block 445. At the end of calibration, foods that are correlated with symptoms are given a point. Foods that are regularly correlated with symptoms will be given multiple points. A relay mechanism built into the program will alert the user that an analysis report is ready. In some embodiments, the user can log into their account to download a report or have the report emailed to themselves or their doctor. In some embodiments, the user's doctor may be the sole report recipient with user consent.

Any block or step singularly or in combination with other blocks or steps can be repeated prior to ending process 400. Moreover, any the blocks or steps shown in process 400 can occur in any order.

Figure 5:
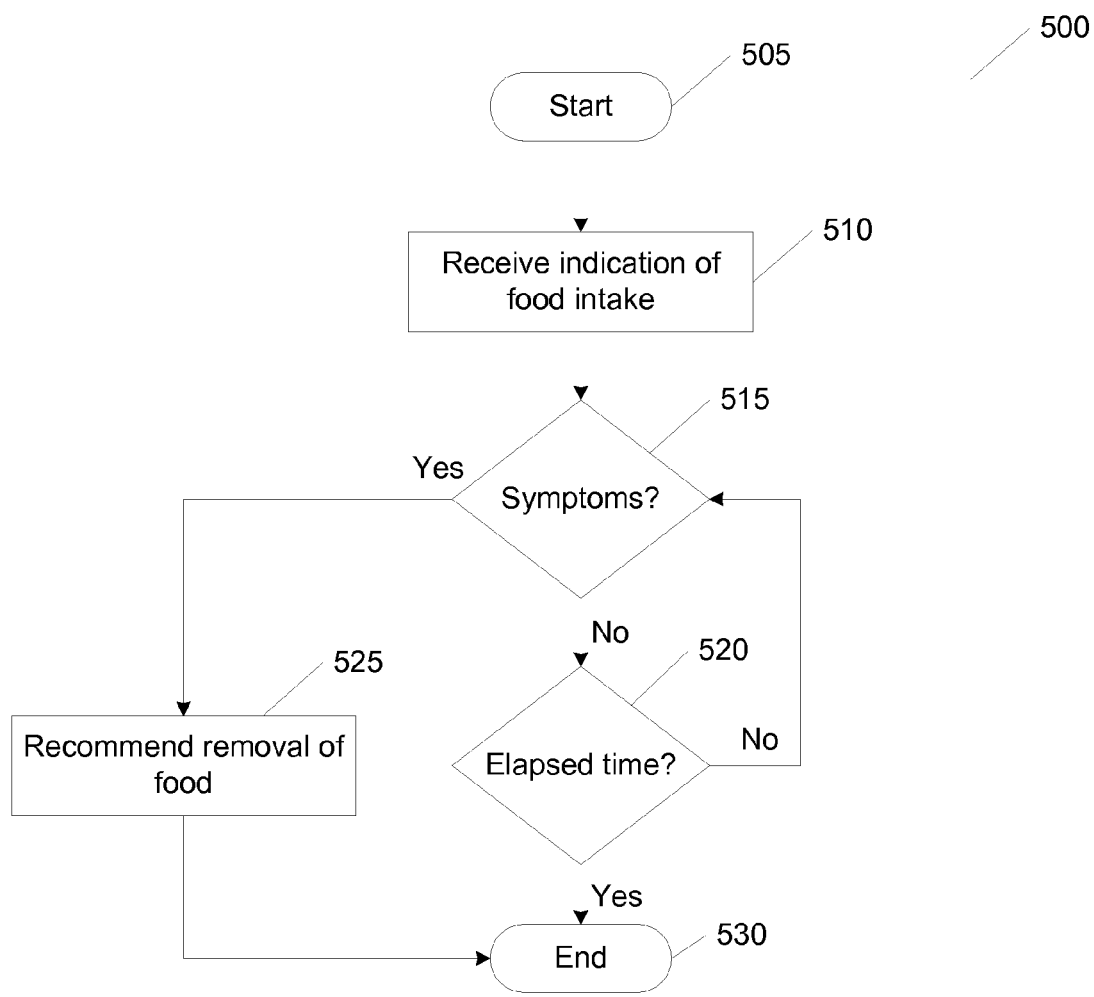
FIG. 5 is a flowchart of a process for anticipation according to some embodiments of the invention.

FIG. 5 is a flowchart of process 500 for anticipation according to some embodiments of the invention. Process 500 can start at block 505. At block 510 an indication of food intake can be received. For example, the indication can be received from a user through user device 105. In some embodiments the indication can be sent from the user device to server 125 through network 110.

At block 515 process 500 can determine whether symptoms occurred following ingestion of the food. If no symptom is found then process 500 can wait 0 to 72 hours at block 520 before moving on. In some embodiments, the time period can be 0-3, 3-6, 3-12, 12-24, 24-72, 24-48, 48-72 and/or 12-72 hours. Otherwise blocks 515 and 520 repeat until a symptom occurs or the predetermined elapsed time occurs. If a symptom occurs, then process 500 can recommend removal of the food at block 525. In some embodiments food can be recommended for removal if the symptom occurs and/or the food has at least one point and/or has points above a threshold number of points.

If no symptom is found, then process 500 ends at block 530. In some embodiments, food may be recommended for removal at block 525 if the food was previously given a point during calibration or if the food has been given more than a threshold number of points.

Process 500 can run for multiple foods in parallel. For instance, if the user enters multiple food items in a single meal or throughout a day, process 500 can operate on each food item independently.

Any block or step singularly or in combination with other blocks or steps can be repeated prior to ending process 500. Moreover, any the blocks or steps shown in process 500 can occur in any order.

Processes 300, 400, and 500 can be repeated after a food item has been removed from a user's diet to test whether removal of the food is correlated with the end of the symptoms.

Figure 6:
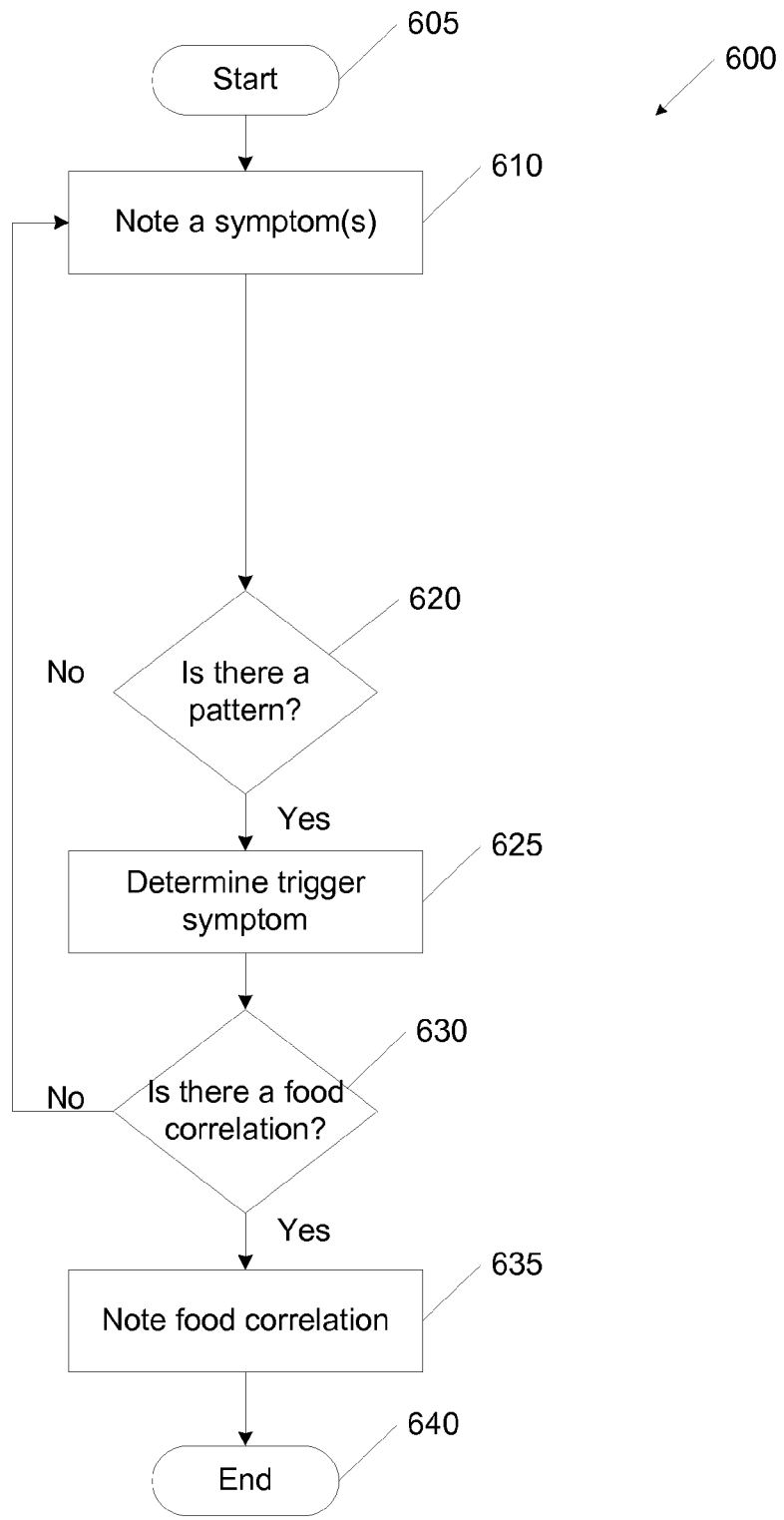
FIG. 6 is a flowchart of a process for tracking symptoms according to some embodiments of the invention.

FIG. 6 is a flowchart of process 600 for tracking symptoms according to some embodiments of the invention. Process 600 starts at block 605. At block 610, a symptom can be noted. In some embodiments the symptom can be noted by receiving an indication from a user, for example, through user device 105, that they are experiencing or have experienced a specific symptom. In some embodiments, the symptom can be noted by analyzing historic user data input from a user through user device 105.

At block 620 process 600 can determine if there is a pattern associated with the symptom. In some embodiments a pattern may occur if a another symptom occurs within 0 to 168 hours after or before the symptom. In some embodiments, the time period can be 0-3, 3-6, 3-12, 12-24, 24-72, 24-48, 48-72, 12-72, 48-120, 48-144, 48-168, 72-120, 72-144 and/or 72-168 hours. A pattern would be any 2-3 symptoms happening in succession of each other. For example, stomach distension followed by an episode of diarrhea. Moreover, in some embodiments, process 600 can determine whether the pattern had been repeated at different periods of time. For example, if a given pattern of symptoms occur during a given week and then reappear three weeks later. Such patterns can be identified and/or can designate a primary and symptom unique to that user.

At block 625 based on the identified symptom pattern, a trigger symptom can be determined. A trigger symptom, for example, can be the first symptom in the symptom pattern. For example, stomach cramps may trigger follow-on symptoms as the body convalesces.

At block 630 a food correlation with the trigger symptom can be determined. For example, a food correlation can be determined by noting any correlation between the intake of a specific food and the occurrence of the trigger symptom within 0 to 72 hours. In some embodiments, the time period can be 0-3, 3-6, 3-12, 12-24, 24-72, 24-48, 48-72, 12-72, 48-120, 48-144, 48-168, 72-120, 72-144 and/or 72-168 hours. Processes 200, 300, and 400 may be rerun removing symptoms from the data set to determine if it changes food correlation.

If there is a food correlation, the food can be given a point at block 635. At block 640 process 600 can end. Process 600 can be repeated any number of times and/or can be used on data collected by a user and stored in a database.

Any block or step singularly or in combination with other blocks or steps can be repeated prior to ending process 600. Moreover, any the blocks or steps shown in process 600 can occur in any order.

Figure 7:
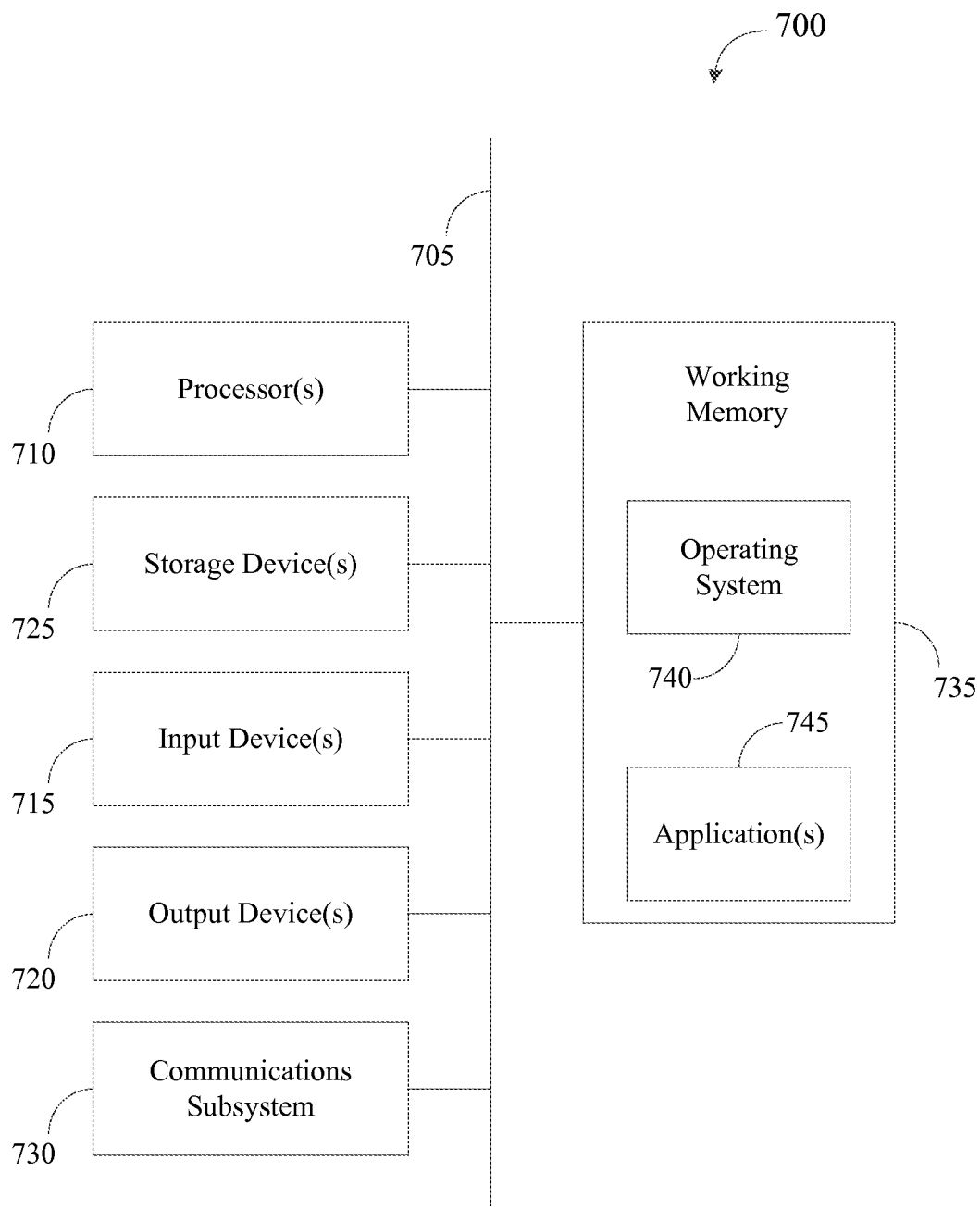
FIG. 7 shows a block diagram of computational system that can be used in the embodiments of the invention.

Some embodiments of the invention can be implemented using a computational system such as a server or computer system. An example of a computational system is shown in FIG. 7. For instance, user devices 105 and server 125 can include one or more computational systems. In some embodiments multiple distributed computational systems can be geographically distributed. Moreover, processes 200, 300, 400, 500 and/or 600 can be executed by one or more such computational systems.

Computational system 700 includes hardware elements that can be electrically coupled via a bus 705 (or may otherwise be in communication, as appropriate). The hardware elements can include one or more processors 710, including without limitation one or more general-purpose processors and/or one or more special-purpose processors (such as digital signal processing chips, graphics acceleration chips, and/or the like); one or more input devices 715, which can include without limitation a mouse, a keyboard and/or the like; and one or more output devices 720, which can include without limitation a display device, a printer and/or the like. Moreover computational system 700 can be or be part of a server or many servers.

The computational system 700 may further include (and/or be in communication with) one or more storage devices 725, which can include, without limitation, local and/or network accessible storage and/or can include, without limitation, a disk drive, a drive array, an optical storage device, cloud storage, storage area network ("SAN"), a solid-state storage device, such as a random access memory ("RAM") and/or a read-only memory ("ROM"), which can be programmable, flash-updateable and/or the like. The computational system 700 might also include a communications subsystem 730, which can include without limitation a modem, a network card (wireless or wired), an infrared communication device, a wireless communication device and/or chipset (such as a Bluetooth device, an 702.6 device, a WiFi device, a WiMax device, cellular communication facilities, etc.), and/or the like. The communications subsystem 730 may permit data to be exchanged with a network (such as the network described below, to name one example), and/or any other devices described herein. In many embodiments, the computational system 700 will further include a working memory 735, which can include a RAM or ROM device, as described above.

The computational system 700 also can include software elements, shown as being currently located within the working memory 735, including an operating system 740 and/or other code, such as one or more application programs 745, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 725 described above.

In some cases, the storage medium might be incorporated within the computational system 700 or in communication with the computational system 700. In other embodiments, the storage medium might be separate from a computational system 700 (e.g., a removable medium, such as a compact disc, etc.), and/or provided in an installation package, such that the storage medium can be used to program a general purpose computer with the instructions/code stored thereon. These instructions might take the form of executable code, which is executable by the computational system 700 and/or might take the form of source and/or installable code, which, upon compilation and/or installation on the computational system 700 (e.g., using any of a variety of generally available compilers, installation programs, compression/decompression utilities, etc.) then takes the form of executable code.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

The terms "invention," "the invention," "this invention" and "the present invention" used in this patent are intended to refer broadly to all of the subject matter of this patent and the patent claims below. Statements containing these terms should not be understood to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the entire specification of this patent, all drawings and each claim.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A method comprising:
   providing a list of a plurality of types of food;
   receiving a plurality of selections of a plurality of types of food from the list of the plurality of types of food, wherein each of the plurality of types of food specify ingestion of a food of the type of food;
   receiving an indication of a plurality of ingestion times;
   recording the plurality of types of food in a database with the plurality of ingestion times;
   providing a listing of a plurality of symptoms;
   receiving a selection of a symptom from the listing of the plurality of symptoms, and receiving an indication of a symptom time;
   recording the selection of the symptom in the database with the time the symptom occurred; and
   analyzing the database to determine whether any of the plurality of types of food are correlated with the occurrence of the symptom, wherein the analyzing comprises assigning a point to each type of food ingested within a predetermined time period prior to the symptom time.

2. The method according to claim 1, wherein the plurality of selections of a plurality of types of food includes the quantity of food ingested.

3. The method according to claim 1, wherein the selection of a symptom from the listing of the plurality of symptoms includes descriptive details of the symptom.

4. The method according to claim 1, wherein the analyzing further comprises determining whether any of the types of foods ingested within zero to seventy-two hours prior to the symptom are correlated with the symptom.

5. The method according to claim 1, wherein the analyzing further comprises determining whether any of the types of foods ingested within zero to seventy-two hours prior to the symptom are known to be correlated with one or more food allergy.

6. The method according to claim 1, further comprising:
   receiving a selection of a second symptom from the listing of the plurality of symptoms, and receiving an indication of a second symptom time;
   recording the selection of the second symptom in the database with the second symptom time; and
   analyzing the database to determine whether any of the plurality of types of food are correlated with the occurrence of the second symptom, wherein the analyzing comprises assigning a point to each type of food ingested within a predetermined time period prior to the second symptom time.

7. The method according to claim 6, further comprising analyzing the symptom and the second symptom to determine whether the second symptom is related to the first symptom.

8. A computer system comprising:
   a processor;
   a database;
   a network interface; and
   a non-transitory computer-readable medium embodying program components that configure the computing system to perform steps comprising:
      providing a list of a plurality of types of food;
      receiving a plurality of selections of a plurality of types of food from the list of the plurality of types of food, wherein each of the plurality of types of food specify ingestion of a food of the type of food;
      receiving an indication of a plurality of ingestion times;
      recording the plurality of types of food in a database with the plurality of ingestion times;
      providing a listing of a plurality of symptoms;
      receiving a selection of a symptom from the listing of the plurality of symptoms, and receiving an indication of a symptom time;
      recording the selection of the symptom in the database with the time the symptom occurred; and
      analyzing the database to determine whether any of the plurality of types of food are correlated with the occurrence of the symptom, wherein the analyzing comprises assigning a point to each type of food ingested within a predetermined time period prior to the symptom time.

9. The computer system according to claim 8, wherein the analyzing further comprises determining whether any of the types of foods ingested within zero to seventy-two hours prior to the symptom are correlated with the symptom.

10. The computer system according to claim 8, wherein the analyzing further comprises determining whether any of the types of foods ingested within zero to seventy-two hours prior to the symptom are known to be correlated with food allergies.

11. The computer system according to claim 8, wherein the non-transitory computer-readable medium embodying program components further configure the computing system to perform the steps comprising:
receiving a selection of a second symptom from the listing of the plurality of symptoms, and receiving an indication of a second symptom time;
recording the selection of the second symptom in the database with the second symptom time; and
analyzing the database to determine whether any of the plurality of types of food are correlated with the occurrence of the second symptom, wherein the analyzing comprises assigning a point to each type of food ingested within a predetermined time period prior to the second symptom time.

12. The computer system according to claim 11, further comprising analyzing the symptom and the second symptom to determine whether the second symptom is related to the first symptom.

13. A computer program product comprising a non-transitory computer-readable medium embodying code executable by a computing system, the code comprising:
providing a user interface listing a plurality of types of foods;
receiving a plurality of selections of a plurality of types of food from the list of the plurality of types of food, wherein each of the plurality of types of food specify ingestion of a food of the type of food;
receiving an indication of a plurality of ingestion times;
recording the plurality of types of food in a database with the plurality of ingestion times;
providing a user interface listing a plurality of symptoms;
receiving a selection of a symptom from the listing of the plurality of symptoms that specifies a particular symptom listed in the listing as affecting the user;
recording the selection of the symptom in the database with the time the symptom occurred; and
analyzing the database to determine whether any of the plurality of types of food are correlated with the occurrence of the symptom, wherein the analyzing comprises assigning a point to each type of food ingested within a predetermined time period prior to the symptom time.

14. The computer program product set forth in claim 13, wherein the code further comprises:
sending the plurality of selections of a plurality of types of food through a network to a server; and
sending the selection of a symptom through a network to the server.

15. The computer program product set forth in claim 13, wherein the code further comprises:
receiving an indication from a server through the network interface recommending removal of a particular food or types of food from the user's diet; and
providing a user interface displaying the a recommendation to remove the particular food or types of food from the user's diet.

16. The computer program product set forth in claim 13, wherein the code further comprises:
analyzing the database to determine whether one or more of the plurality of selections of a plurality of types of food are correlated with the occurrence of the selection of a symptom.

17. A method comprising:
identifying a first digestive symptom in a database comprising a plurality of symptoms entered by a user and the time the symptom occurred;
identifying a second digestive symptom in the database, wherein the second symptom occurred in time after the first symptom and wherein the second digestive symptom is different than the first digestive symptom;
determining whether a pattern exists between the second digestive symptom and the first symptom; and
determining whether the first digestive symptom triggers the second digestive symptom.

18. The method according to claim 17, wherein the determining whether a pattern occurs further comprises determining whether the second symptom follows the first symptom elsewhere in the database.

19. The method according to claim 17, wherein the determining whether a pattern occurs further comprises determining whether the second symptom occurs with zero to seventy-two hours after the first symptom.

20. The method according to claim 17, further comprising:
identifying a third symptom in the database, wherein the third symptom occurs after the second symptom; and wherein the determining whether a pattern exists, further comprises determining whether a pattern exists between the third symptom, the second symptom and the first symptom.

21. The method according to claim 17, further comprising identifying whether a type of food is correlated with either or both the first symptom or the second symptom.

* * * * *